United States Patent
Frater-Schroder et al.

(10) Patent No.: US 7,135,198 B2
(45) Date of Patent: Nov. 14, 2006

(54) PREPARATION FOR ORAL ADMINISTRATION

(75) Inventors: Marijke Frater-Schroder, Winterthur (CH); Georg Frater, Winterthur (CH)

(73) Assignee: Bogar AG, Zurich (CH)

( * ) Notice: Subject to any disclaimer, the term of this patent is extended or adjusted under 35 U.S.C. 154(b) by 0 days.

(21) Appl. No.: 10/259,910

(22) Filed: Sep. 30, 2002

(65) Prior Publication Data

US 2003/0068358 A1    Apr. 10, 2003

(30) Foreign Application Priority Data

Oct. 1, 2001   (EP)   ................... 01123561

(51) Int. Cl.
*A01N 65/00* (2006.01)
*A61K 49/00* (2006.01)
*A61K 8/97* (2006.01)
*A61K 9/14* (2006.01)

(52) U.S. Cl. ............... 424/725; 424/9.31; 424/58; 424/489; 424/730; 424/732; 424/734; 424/737; 424/746; 424/748

(58) Field of Classification Search ........... 424/737, 424/9.31, 683, 684, 439, 442, 730, 732, 734, 424/746, 748, 725, 58, 489; 514/949; 510/334
See application file for complete search history.

(56) References Cited

U.S. PATENT DOCUMENTS

| 5,863,581 | A | * | 1/1999 | Barrett et al. |
| 6,217,818 | B1 |  | 4/2001 | Collette et al. |
| 6,287,576 | B1 | * | 9/2001 | Bgatov et al. |
| 6,511,683 | B1 | * | 1/2003 | Gahler et al. |

FOREIGN PATENT DOCUMENTS

| CN | 1150890 A | * | 6/1997 |
| DE | 1 040 183 |  | 10/1958 |
| DE | 37 44571 A1 |  | 7/1989 |
| DE | 19751181 A1 | * | 5/1999 |
| EP | 000537402 A1 | * | 10/1991 |
| EP | 0 721 741 A1 |  | 7/1996 |
| EP | 1 129 627 A1 |  | 9/2001 |
| EP | 1 132 009 A1 |  | 9/2001 |
| FR | 2 703 242 |  | 10/1994 |
| FR | 2 743 722 |  | 7/1997 |
| GB | 485188 |  | 5/1938 |
| JP | 56018554 A | * | 2/1981 |
| JP | 2001046017 A | * | 2/2001 |
| WO | 96/08168 |  | 3/1996 |
| WO | 96/22028 |  | 7/1996 |

OTHER PUBLICATIONS

Green, J. G. The Herbal Medicine-Maker's Handbook: A Home Manual (2000). The Crossing Press, USA, pp. 146-154 and 275-285.*
Galvano, F. et al., Journal of Food Protection (Jan. 2001), 64(1): 120-131. Dietary strategies to counteract the effects of mycotoxins: A review.9.*
Ramos, A.-J. et al., Journal of Food Protection (1996), 59(6): 631-641. Prevention of toxic effects of mycotoxins by means of nonnutritive adsorbent compounds.*
Receuil de Medecine Veterinaire, vol. 166, (1) (1990), pp. 21-27.
W. Heinze and D. Oschika, Tierarztliche Umschau, 55, 621-627 and 678-683 (2000).

* cited by examiner

*Primary Examiner*—Michele Flood
(74) *Attorney, Agent, or Firm*—Oliff & Berridge, PLC

(57) ABSTRACT

A preparation for oral administration, in which plant material is comminuted and treated by mixing thoroughly with an extractant. After mixing, porous inorganic particles are added to the resulting suspension, thoroughly mixed with mixture and dried. The preparation provides a homogeneous distribution of the active ingredient as well as long stability and good bioavailability of the active ingredient.

22 Claims, No Drawings

PREPARATION FOR ORAL ADMINISTRATION

BACKGROUND OF THE INVENTION

1. Field of the Invention

The present invention relates to a preparation for oral administration.

2. Description of Related Art

The use of clay in the animal feed industry has been known for a relatively long time. Receuil de Médecine Vétérinaire, Vol. 166 (1) (1990), at pp. 21–27, reviews the use of various types of clay in the feed industry.

Bentonite and smectite are used as feed additives for calves and pigs and have a beneficial effect on diarrhea and in pH regulation (W. Heinze and D. Oschika, Tierärztliche Umschau, 55, 621–627 and 678–683 (2000).

WO 96/08168 describes a feed additive comprising a choline compound, fatty acids and a carrier, it being possible for the carrier to consist of clay.

WO 96/22028 describes a process for producing a medicament for animals in which the active ingredient is contained in a cohesive gel.

EP 0 721 741 A1 describes the use of acid-activated montmorillonite clay in mycotoxin-contaminated feed.

FR 2 743 722 describes a clay-containing preparation for topical treatment of acne.

FR 2 703 242 describes a preparation containing clay and essential oils for topical applications.

The function of the nonspecific immune system, and thus the susceptibility of animals and humans to viral or bacterial infections, may be respectively considerably influenced and increased by genetic defects or by factors related to nutrition, aging or the environment.

SUMMARY OF THE INVENTION

The object of the present invention is to provide a preparation which has a homogeneous distribution of active ingredient, a long stability of active ingredient and good bioavailability.

A specific object of the present invention is to provide a preparation that assists the nonspecific immune system and additionally has a long stability of active ingredient and good bioavailability.

The objects are achieved by a preparation in which comminuted plant material is mixed with an extractant and porous inorganic particles. Further advantageous embodiments of the invention are evident from the dependent claims and the description.

DETAILED DESCRIPTION OF THE PREFERRED EMBODIMENTS

The preparation of the invention for oral administration is obtainable by a) comminuting plant material, b) treating the comminuted plant material with an extractant, c) thoroughly mixing the comminuted plant material and the extractant, d) adding porous inorganic particles to the suspension obtained in step c), e) thoroughly mixing the mixture obtained in step d) and f) drying the mixture obtained in step e).

The presence of comminuted plant material and the porous inorganic particles means that the preparation of the invention comprises two carriers. The redistribution of some substances from one carrier, namely from the comminuted plant material, to the other carrier, i.e. to the porous inorganic particles, results in optimal loading of both carriers. This stabilizes the preparation of the invention, and the bioavailability of the substances is better.

The porous inorganic particles present in the preparation of the invention preferably comprise clay. The inorganic particles are particularly preferably selected from the group of bentonite, kaolinite, smectite, montmorillonite, sepiolite and natural zeolites. The porous nature of these particles makes uptake of the extracts of the plant material possible. The inorganic particles preferably have a size of up to 500 µm, preferably up to 250 µm and particularly preferably up to 100 µm.

The term plant material means in the present invention the whole plants or parts of plants such as roots, stalks, leaves or flowers. The plant material is preferably selected from the group of

| Family | Plant name | Plant material | Common name |
| --- | --- | --- | --- |
| Asteraceae | Achillea Millefolium | *Millefolii herba* | Milfoil |
| Apiaceae | *Apium graveolens* | *Apii graveolentis radix* | Celery root |
| Bursaraceae | *Boswellia serrata* | *Boswellia serrata* | Boswellia resin |
| Papaveraceae | *Chelidonium majus* | *Chelidonii herba* | Greater celandine |
| Apiaceac | *Centella asiatica* | *Centellae asiaticae herba* | Indian pennywort |
| Bruseraceae | *Commiphora molmol* | *Myrrha* | Myrrh |
| Rosaceae | *Crataegus monogyna* and/or *laevigata* | *Crataegi fructus* | Hawthorn berries |
| Asteraceae | *Cynara scolymus* | *Cynarae folium* | Artichoke leaves |
| Asteraceae | *Echinacea purpurea* | *Echinaceae purpureae radix* | Sunflower root |
| Fabaceae | *Trigonella foenum graecum* | *Foenugraeci semen* | Fenugreek seeds |
| Ginkgoaceae | *Ginkgo biloba* | *Ginkgo biloba folium* | Ginkgo leaves |
| Hamamelidacaeae | *Hamamelis virginiana* | *Hamamelidis folium* | Hamamelis leaves |
| Hamamelidacaeae | *Hamamelis virginiana* | *Hamamelidis cortex* | Hamamelis bark |
| Pedaliaceae | *Harpagophytum* | *Harpagophyti radix* | Devil's claw root |

-continued

| Family | Plant name | Plant material | Common name |
|---|---|---|---|
| | procumbens | | |
| Hypericaceae | Hypericum perforatum | Hyperici herba | St John's wort |
| Juglandaceae | Juglans regia | Juglandis folium | Walnut leaves |
| Lamiaceae | Leonurus cardiaca | Leonun cardiaceae herba | Motherwort |
| Lamiaceae | Lycopus europaeus | Lycopi herba | Gypsywort |
| Myrtaceae | Melaleuca Alterniflora | Melaleucae aetheroleum | Melaleuca oil |
| Fabaceae | Ononis spinosa | Ononidis radix | Restharrow root |
| Lamiaceae | Origanum vulgare | Origani herba | Oregano |
| Passifloraceae | Passiflora incarnata | Passiflorae herba | Passion-flower |
| Piperaceae | Piper methysticum | Kava-Kava Rhizoma | Kava-kava root |
| Rosaceae | Pontentilla anserine | Anserinae Herba | Silverweed |
| Primulaceae | Primula veris | Primulae radix | Primrose root |
| Fagaceae | Quercus robur | Quercus cortex | Oak bark |
| Krameriaceae | Krameria triandra | Ratanhiae radix | Ratanhia root |
| Saxifragaceae | Ribes nigrum | Ribis nigri folium | Blackcurrant leaves |
| Fabaceae | Robinia pseudacacia | Robinia fructus | Black locust |
| Lamiaceae | Salvia officinalis | Salviae folium | Sage leaves |
| Caesalpiniaceae | Cassia senna | Sennae fructus, folium | Senna leaves, senna pods |
| Asteraceae | Solidago virgaurea and/or Canadensis | Solidaginis herba | Golden rod |
| Asteraceae | Silybum marianum | Cardui mariane fructus | Milk thistle fruit |
| Urticaceae | Urtica dioica | Urticae folium | Stinging nettle leaves |
| Urticaceae | Urtica dioica | Urticae radix | Stinging nettle root |
| Ericaceae | Vaccinium vitis idaea | Vitis idaeae folium | Cowberries/foxberries |
| Valerianaceae | Valeriana officinalis | Valerianae radix | Valerian root |
| Violaceae | Viola tricolor | Violae tricoloris herba | Heartsease |
| Loranthaceae | Viscum album | Visci herba | Mistletoe |
| Verbenaceae | Vitex agnus castus | Agni casti fructus | Chaste berry |
| Lichenes | Cetraria islandica | Lichen islandicus | Icelandic moss |
| Lichenes | Cetraria tenuifolia | Lichen islandicus | Icelandic moss |
| Lichenes | Cetraria ericetorum | Lichen islandicus | Icelandic moss |

The abovementioned plants or parts of plants can be used alone or as combination of a plurality of plants.

Before the processing, the plant material is preferably dried. The plant material is comminuted in step a) of the process described above by grinding, chopping, dismembering or another suitable process. The comminuted plant material has a size of up to 1000 μm, preferably a size of up to 710 μm. The maximum distribution of the comminuted plant material is preferably in the range from 200 to 300 μm, preferably at 250 μm. The comminuted plant material therefore preferably has approximately the same size as the porous inorganic particles.

Suitable extractants are all the organic solvents known to the skilled worker, mixtures of solvents and mixtures of solvents with water, which have the ability to dissolve substances out of the plant material. Alcohols are preferred, but pure ethanol or ethanol/water mixtures in ratios of from 75:25 to 99:1% are particularly preferred. Further suitable extractants are, for example, methanol or methylene chloride.

The comminuted plant material is added to the extractant in step b). Components are extracted from the plant material in step c) through the intimate mixing of the comminuted plant material and the extractant. The inorganic particles are subsequently added to the suspension obtained in step c). The porous inorganic particles, the plant material and the extracts thereof are then thoroughly mixed, resulting in a uniform mixture. The abovementioned mixture of the porous inorganic particles, the plant material and the extracts thereof is dried after mixing. The moisture content is preferably less than 5% based on the total weight of the preparation. The ethanol content of the preparation of the invention should be as low as possible and is preferably less than 0.5% based on the total weight of the preparation. The preparation of the invention is preferably in the form of a powder. Other extractants such as methanol or methylene chloride must be substantially removed.

The ratio of the porous inorganic material to the plant material in the preparation of the invention is in the range from 0.33:1 to 10:1, preferably in the range from 1:1 to 5:1 and particularly preferably in the range from 2:1 to 3:1.

The use of ethanol or of an ethanol/water mixture in step b) of the process described above also achieves an antiseptic effect. This, and the removal of water, additionally increases the long-term stability of the product in the dry state without the need for time-consuming or costly stabilization measures. The preparation of the invention has a stability of at least 2 years.

The presence both of the comminuted plant material and of the extracts thereof in the preparation of the invention means that none of the constituents of the plant material are lost. In addition, the preparation of the invention displays an exceptionally good bioavailability because components of the plant material which are otherwise available to the body only with difficulty are made more available by the inorganic porous material. At the same time, other components in the plant material may in turn promote or inhibit the absorption of certain other components. The interplay of the porous inorganic particles, the comminuted plant material and the extracts thereof achieves an exceptionally good therapeutic efficacy.

For example, the preparation described in example 5 has an exceptionally beneficial effect both on the nonspecific immune system and on the progress of viral and bacterial infections. The complex interplay of all the constituents of this preparation of the invention results in a broad multifunctional therapeutic efficacy, leading to an overall effect which is greater than the sum of all the individual effects, i.e. synergistic effects are present.

The surprisingly good effect of the preparation described in example 5 derives inter alia from the good bioavailability of the individual components and from the fact that the active components take effect at different points in the healing process and the defense system. This preparation of the invention promotes microbial defense in this way both when the immune system is weakened and when it is intact. The interaction of the porous inorganic particles, the plant material and the extracts thereof has a significantly beneficial and synergistic effect on the nonspecific defense system and on the healing process in refractory and/or chronic airway disorders.

This preparation of the invention, which comprises *Echinacea purpurea*, is particularly suitable for strengthening the body's own immune system and assists in curing refractory and/or chronic airway disorders. It is additionally suitable for the treatment of seasonal and age-related states of weakness of the immune system, seasonal airway disorders such as colds, kennel cough, bronchitis, pharyngitis, tonsillitis. No side effects were observable after intake of this preparation of the invention.

Preferably, one gram of the preparation described in example 5 is administered per 10 kg of bodyweight to an animal or a person in the moist feed or food. In the case of treatment of the abovementioned disorders, this preparation of the invention should be taken regularly for at least two weeks, but preferably four to eight weeks. The preparation of the invention can, however, also be administered prophylactically and thus ensure an improved general wellbeing.

With other plant material it is possible for example to treat dyspetic symptoms or gastrointestinal and biliary disorders. The preparation of the invention thus represents an effective remedy.

The preparation of the invention is preferably fed to mammals and aquatic animals. Particular preference is given to pets such as dogs, cats, fish, rabbits, hares and birds, or breeding animals such as calves, cattle, cows, horses, sheep, pigs, chickens, shrimps and fish. The preparation of the invention also increases the general wellbeing of people after oral intake.

The preparation of the invention is preferably mixed as powder or granules directly with the feed or else incorporated into the feed during manufacture. In this connection, a large number of different possibilities for administration are possible, such as, for example, dry feed, biscuits etc. An alternative possibility is also for the preparation of the invention to be incorporated into a food supplement or to be used as such. The preparation of the invention may, besides the constituents mentioned above, also comprise the additions customary in pharmaceutical preparation.

EXAMPLES

The following examples serve to illustrate the invention without restricting the scope thereof.

Example 1

Raw materials employed
*Hyperici herba*: (ground to <0.25 mm)
Sepiolite
Ethanol 96%

300 g of ground plant material are placed in a container and 450 g of ethanol 96% are added. The mixture is stirred for 1 hour. Then add 900 g of sepiolite and mix thoroughly. Dry the mixture in a vacuum oven at 40° C. for 48 hours. Pass through a 0.355 mm sieve and again mix thoroughly.
Yield: 1.12kg
Indication: antiviral In analogy to the above example, the plants listed in the above table were employed in place of *hyperici herba* and processed analogously.

Example 2

Raw materials employed
Quercus cortex: (ground to <1 mm)
Sepiolite
Methanol 95%

300 g of ground plant material are placed in a container and 450 g of methanol 95% are added. The mixture is stirred for 1 hour. Then add 600 g of sepiolite and mix thoroughly. Dry the mixture in a vacuum oven at 40° C. for 48 hours. Pass through a 0.71 mm sieve and again mix thoroughly.
Yield: 820 g
Indication: astringent for diarrhea Example 3

Raw materials employed
*Salviae officinalis* folium:: (ground to <1 mm)
Sepiolite
Ethanol 96%

300 g of ground plant material are placed in a container and 450 g of ethanol 96% are added. The mixture is stirred for 1 hour. Then add 300 g of sepiolite and mix thoroughly. Dry the mixture in a vacuum oven at 40° C. for 48 hours. Pass through a 0.71 mm sieve and again mix thoroughly.
Yield: 545 g
Indication: dyspeptic symptoms, gastrointestinal/biliary disorder.

Example 4

Raw materials employed
*Cynarae folium*
Sepiolite
Ethanol 96%

1.25 kg of plant powder is placed in a 6 l tank, and 1.5 l of ethanol at 75° C. are poured on. The temperature after mixing is about 46° C. Cover the mixture with foil and leave to stand for 1 hour. Then add 1.25 kg of sepiolite and mix very thoroughly. The product is distributed on a polyethylene sheet and dried at room temperature under a hood for 20 hours. The product is passed through a 1 mm sieve and dried in a vacuum oven at max. 45° C. for 30 hours.
Yield: 2.41 kg
Indication: cholagogue, dyspeptic symptoms, gastrointestinal/biliary disorders

Example 5

Raw materials employed
*Echinacea purpurea*
Sepiolite
Ethanol 96%

1.25 kg of plant powder is placed in a 6 l tank, and 1.5 l of ethanol at 75° C. are poured on. The temperature after mixing is about 46° C. Cover the mixture with foil and leave to stand for 1 hour. Then add 2.5 kg of sepiolite and mix very thoroughly. The product is distributed on a polyethylene sheet and dried at room temperature under a hood for 20 hours. The product is passed through a 1 mm sieve and dried in a vacuum oven at max. 45° C. for 30 hours.
Yield: 3.5 kg
Indication: general immunostimulant, kennel cough The abovementioned preparation was tested for its stability according to the Pharmacopeia inter alia with the lead substances Dodeca (2E,4E,8Z,10E)-tetraencarboxylic acid isobutylamide and zichloric acid.

Example 6

Clinical Study

An open multicenter controlled clinical study was carried out in order to demonstrate the efficacy and tolerability of the preparation described in example 5 for dogs on treatment of chronic and/or recurrent infections of the airways (pharyngitis/tonsillitis, bronchitis, kennel cough) and/or in underdeveloped young animals. Each animal served as its own control element for the chronic illnesses. The chronic condition according to the patient's history was recorded in the CRF (trial report).

Forty-one (41) dogs were entered in this study. This was the intention to treat (ITT) population. The treatment was assessed in relation to tolerability and efficacy after four weeks in thirty-nine (39) dogs and also after eight weeks of treatment in thirty-eight (38) dogs. These formed the acceptable patient population (PP). The dogs were selected by six veterinarians practicing in Switzerland with the written declaration of consent by the animals' owners. The selection was based upon compatibility with inclusion/exclusion criteria and a clinical examination as set forth in the study protocol. Only one dog was unable to complete the study because he developed a musculoskeletal pathology, unrelated to the study, which required steroid therapy.

Forty-one (41) dogs which had been diagnosed with one or more of the following chronic and/or recurrent disorders of the airways were included in the study: kennel cough, bronchitis and pharyngitis/tonsillitis. Although recurrent pneumonia was likewise a criterion for inclusion, no dogs with this pathology were included. A chronic pathology is defined in the study protocol as a disorder which is not expected to improve untreated within eight weeks. Three underdeveloped young dogs were also included in the study. All the animals were examined by the investigating veterinarian before the therapy and after treatment had lasted four and eight weeks. 30 animals were additionally examined after 15±3 days. At each examination, the occurrence and severity of the following clinical parameters and symptoms was well recorded: bodyweight, temperature (rectal), condition of fur, appetite, lethargy, discharge from eyes (clear and purulent), discharge from nose (clear and purulent), cyanosis, enlargement of lymph nodes, dehydration, cough, dyspnea and lung sounds (moist and dry). Blood samples for hematological and biochemical investigations were taken before the start of therapy and after treatment had lasted eight weeks. The animal's owner administered the preparation of the invention for eight weeks in a dosage of 0.1 g/kg of bodyweight mixed with moist feed. The delivery of medicament was recorded by the animal's owner in a "animal's owner's diary".

The investigating veterinarian made a global assessment of the efficacy of the treatment for each dog after four and eight weeks, on the basis of the changes in the symptoms, as "very good", "good", "moderate" or "inadequate". The secondary parameters of efficacy were assessed by assessing the severity of the symptoms of condition of the fur, appetite, lethargy, discharge from the eyes (clear and purulent), discharge from the nose (clear and purulent), cyanosis, enlargement of lymph nodes, dehydration, cough, dyspnea and lung sounds (moist and dry) before and after the treatment with the preparation of the invention. The veterinarian made a global assessment of the tolerability of the treatment as "very good", "good", "moderate" or "unsatisfactory" for each dog after the treatment had lasted four and eight weeks on the basis of the occurrence and nature of all the unwanted effects.

Results

The data on the efficacy for dogs with pharyngitis/tonsillitis, bronchitis, kennel cough and/or underdeveloped young animals were analyzed using the SAS statistics package version 6.12. The data of 39 of the 41 dogs entered in the study were analyzed because two dogs (numbers 8 and 39) required treatment with antibiotics during the study and therefore were excluded from the analysis. After treatment had lasted eight weeks, the data for 38 dogs were analyzed, because dog No. 29 was excluded from the study as a result of a clinical pathology unconnected with the study and requiring treatment with steroids. A statistically significant efficacy was demonstrated after the treatment had lasted both four and eight weeks. In 92.3% of the cases (36/39), the efficacy was assessed after the treatment with the preparation of the invention had lasted four weeks as "good" or "very good" with a 95% confidence interval between 88% and 102%. The global efficacy after the treatment had lasted eight weeks was assessed as "good" or "very good" in 94.8% of the cases (36/38) with a 95% confidence interval between 88% and 102%.

It was possible with the aid of the Bowker test to demonstrate a highly significant ($p<0.01$) reduction in the severity of all the following main symptoms in this study after the treatment had lasted both four and eight weeks: condition of the fur, appetite, lethargy, discharge from the eyes (purulent), discharge from nose (clear), enlargement of lymph nodes, cough (dry), dyspnea and lung sounds (dry). A significant reduction in the clear discharge from the eyes was shown after the treatment had lasted four ($p<0.04$) and eight weeks ($p<0.01$). A statistically significant reduction in the body temperature (measured rectally) was detected after the treatment had lasted both four and eight weeks.

The primary assessment of the tolerability was based on the occurrence and nature of unwanted effects. No animals died during this study. An unwanted effect was found only in one dog (1/39). The diagnosis for this animal (No. 8) was bronchitis and pharyngitis/tonsillitis. During treatment with the preparation of the invention there was an initial improvement. On day 26, the cough became very much worse and was recorded as a serious unwanted effect. In the veterinarian's view, kennel cough had occurred due to superinfection. The animal was prescribed an antibiotic (SYNULOX®, Pfizer Ltd) for eight days. Treatment with the preparation of the invention was continued during this period. The dog's condition improved rapidly after administration of the antibiotic. Although this animal should have been excluded from this study because of the concurrent treatment of antibiotics, the study monitor agreed to him remaining in the study (deviation 3). No other unwanted effects occurred in this animal during the eight weeks of treatment. The occurrence of the described unwanted effect cannot clearly be attributed to the treatment with the preparation of the invention.

The systemic tolerability of the preparation of the invention was demonstrated in the hematological and biochemical findings before and after eight weeks of treatment. The global tolerability of the product was assessed as "good" or "very good" in 100% of the cases (39/39) after four weeks and as "good" or "very good" in 100% of the cases (38/38) after eight weeks.

CONCLUSIONS

This study has shown that the preparation of the invention, administered orally in a dose of 0.1 g/kg of bodyweight for four to eight weeks is tolerated by dogs and is effective for the treatment of chronic and/or recurrent infections of the airways, including pharyngitis/tonsillitis, bronchitis and kennel cough. After treatment with the preparation of the invention had lasted four weeks, a statistically significant (p<0.01) reduction in the severity of the symptoms or elimination of symptoms of chronic and/or recurrent infections of the airways was demonstrated, and was still clearly present after eight weeks.

What is claimed is:

1. A preparation for oral administration, wherein the preparation is produced by a process comprising:
    a) comminuting plant material,
    b) treating the comminuted plant material with an extractant,
    c) thoroughly mixing the comminuted plant material and the extractant to form a suspension,
    d) adding porous clay to the suspension obtained in step c) to form a mixture,
    e) thoroughly mixing the mixture obtained in step d) and
    f) drying the mixture obtained in step e).

2. The preparation according to claim 1, wherein the clay is selected from the group consisting of bentonite, smectite, montmorillonite, kaolinite, and sepiolite.

3. A preparation according to claim 1, in which the plant material is selected from the group consisting of *Echinacea purpurea, Crataegus monogyna* and/or *laevigata, Melaleuca alternfolia, Solidago virgaurea* and/or *canadensis, Ononis spinosa, Boswellia serrata, Piper methysticum, Cynara scolymus, Trigonellafoenum graecum, Passiflora incarnata, Juglans regia, Achillea millefolium, Cassia senna, Vitex agnus castus, Harpagophytum procumbens, Viscum album, Robinia pseudacacia, Valeriana officinalis, Hamamelis virgin iana, Quercus robur, Potentilla anserina, Hypericum perforatum, Salvia officinalis, Vaccinium vitis idaea, Cetraria islandica, Cetraria tenuifolia, Cetraria ericetorum* and *Silybum marianum*.

4. A preparation according to claim 3, wherein the plant material comprises *Echinacea purpurea*.

5. A feed additive comprising the preparation according to claim 1.

6. A feed comprising the preparation according to claim 1.

7. A process for producing a preparation for oral administration, comprising:
    a) comminuting plant material,
    b) treating the comminuted plant material with an extractant,
    c) thoroughly mixing the comminuted plant material and the extractant to form a suspension,
    d) adding porous clay to the suspension obtained in step c) to form a mixture,
    e) thoroughly mixing the mixture obtained in step d) and
    f) drying the mixture obtained in step e).

8. The process according to claim 7, wherein the plant material is *Echinacea purpurea*.

9. The process according to claim 7, wherein the extractant is an alcohol.

10. The process according to claim 7, wherein the clay is *sepiolite*.

11. The process according to claim 7, wherein the plant material is *Echinacea purpurea*, the extractant is an alcohol, and the clay is *sepiolite*.

12. A preparation for oral administration, comprising a comminuted plant material, an extractant, and porous clay mixed in a suspension to form a mixture wherein the mixture is dried after the comminuted plant material, the extractant and the porous clay are mixed.

13. The preparation according to claim 12, wherein the clay is selected from the group consisting of *bentonite, smectite, montmorillonite, kaolinite*, and *sepiolite*.

14. The preparation according to claim 12, in which the plant material is selected from the group consisting of *Echinacea purpurea, Crataegus monogyna* and/or *laevigata, Melaleuca alternifolia, Solidago virgaurea* and/or *canadensis, Ononis spinosa, Boswellia serrata, Piper methysticum, Cynara scolymus, Trigonellafoenum graecum, Passiflora incarnata, Juglans regia, Achillea millefolium, Cassia senna, Vitex agnus castus, Harpagophytum procumbens, Viscum album, Robinia pseudacacia, Valeriana officinalis, Hamamelis virginiana, Quercus robur, Potentilla anserina, Hypericum perforatum, Salvia officinalis, Vaccinium vitis idaea, Cetraria islandica, Cetraria tenuifolia, Cetraria ericetorum* and *Silybum marianum*.

15. The preparation according to claim 14, comprising *Echinacea purpurea*.

16. A feed additive comprising the preparation according to claim 12.

17. A feed comprising the preparation according to claim 12.

18. The preparation according to claim 1, wherein the extractant is an alcohol.

19. The preparation according to claim 18, wherein the extractant is ethanol.

20. The process according to claim 9, wherein the extractant is ethanol.

21. The preparation according to claim 12, wherein the extractant is an alcohol.

22. The preparation according to claim 21, wherein the extractant is ethanol.

* * * * *